United States Patent [19]
Seiden et al.

[11] Patent Number: 5,426,593
[45] Date of Patent: * Jun. 20, 1995

[54] GAS CONTENT MEASUREMENT

[76] Inventors: Louis W. Seiden, 11100 Rosemont Dr., N. Bethesda, Md. 20852; Marc J. Epstein, 14 Beach Ave., Leonardo, N.J. 07737; Steven A. Seiden, 3701 Lail Ct., Raleigh, N.C. 27606

[*] Notice: The portion of the term of this patent subsequent to Jun. 15, 2010 has been disclaimed.

[21] Appl. No.: 48,641

[22] Filed: Apr. 2, 1993

Related U.S. Application Data

[63] Continuation-in-part of Ser. No. 656,713, Feb. 19, 1991, Pat. No. 5,220,513.

[51] Int. Cl.$^6$ ............................................. G01N 7/00
[52] U.S. Cl. .................................. 364/496; 73/19.01; 73/19.06; 73/52
[58] Field of Search .............. 364/500, 499, 498, 498, 364/496, 571.05; 73/19.01, 19.06, 52, 863.85, 864.74

[56] References Cited

U.S. PATENT DOCUMENTS

| | | | |
|---|---|---|---|
| 4,281,536 | 8/1981 | Kraft et al. | 73/52 |
| 4,555,935 | 12/1985 | Elert | 73/52 |
| 4,578,762 | 3/1986 | Wong | 364/497 |
| 4,607,342 | 8/1986 | Seiden et al. | 364/558 |
| 4,674,061 | 6/1987 | Diskowski et al. | 364/558 X |
| 4,730,112 | 3/1988 | Wong | 250/343 |
| 4,731,732 | 3/1988 | Warchol et al. | 364/497 X |
| 4,733,555 | 3/1988 | Franks | 73/52 X |
| 4,926,681 | 5/1990 | Fitzpatrick | 73/52 |
| 4,928,539 | 5/1990 | Champseix et al. | 73/863.85 X |
| 5,029,103 | 7/1991 | Corbett | 364/497 |
| 5,056,034 | 10/1991 | Rucki et al. | 364/500 X |
| 5,199,297 | 4/1993 | Lin et al. | 73/52 |
| 5,220,513 | 6/1993 | Seiden et al. | 364/500 |

*Primary Examiner*—Edward R. Cosimano

[57] ABSTRACT

This invention is directed to a device which measures the oxygen component of a beverage gas using a specific oxygen probe, ultrasonic degassing, a special valving technique, and microprocessor based software. The measurement is made in the gaseous state in a two chamber system. The device is controlled by an electronic console that is built around a microprocessor which sequences and times the valves, receives the data from the oxygen probe and its accompanying temperature compensation circuit, and displays the data. An alternative method is to use several chambers and one pass. Additional chambers may be used to increase the speed of the test, control interferences, or aid in identifying gases other than the oxygen component. The device may also have an interface piercing head manifold that allows $CO_2$ and oxygen to be tested in the same container and in one preparation. The invention also relates to specific gas measurements with non-specific type measurements and the general techniques can be applied to environmental problems that involve oxygen demand and respiration of bacteria.

25 Claims, 12 Drawing Sheets

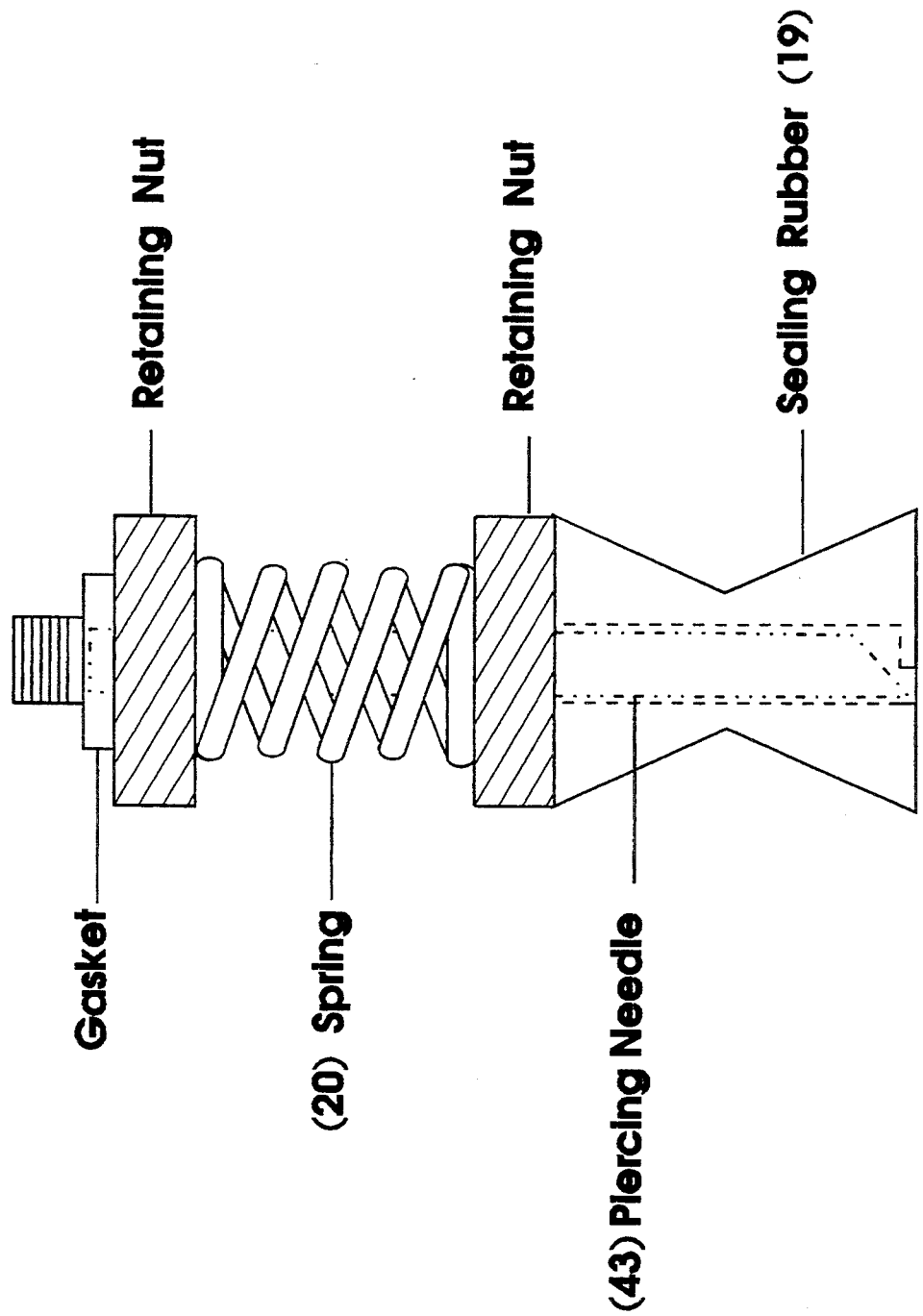

GAS CONTENT MEASUREMENT

This is continuation-in-part application of U.S. patent application Ser. No. 07/656,713, filed Feb. 19, 1991, now issued as U.S. Pat. No. 5,220,513.

BACKGROUND OF THE INVENTION

1. FIELD OF THE INVENTION

This invention relates to the measurement of the gas content of a closed or sealed container after degassing by a special valving technique, a gas specific probe or probes, and microprocessor based software.

2. DESCRIPTION OF THE BACKGROUND

AIR CONTENT

Air content—via the oxygen component of air—in a liquid is a quantity that is of interest to the canning industry in general and the beverage industry in particular. The current generally accepted method for measuring the air content in a beverage liquid (usually carbonated) is by a non-electronic chemical technique. The conventional method for measuring the air content in a carbonated beverage is a chemical test using a hydroxide solution. The hydroxide solution is used to absorb $CO_2$ and while a 10% solution will work, a stronger solution will function more rapidly and is less quickly diluted by beer which works up the Burrette. After the test is finished, the valve assembly should be thoroughly flushed with water to remove the sample (Zahm Practical Testing Instruments 15th Edition, pages 12 and 13).

Although it might be theoretically possible to make a measurement in the liquid, such a measurement is both difficult mechanically and difficult to analyze. The interpretation of the data because of solubility problems which are a function of additives (wanted and unwanted) would be very complex and troublesome. Temperature and pressure variations are also a problem. Air is primarily nitrogen and oxygen in approximately a 4 to 1 ratio (80% nitrogen, 20% oxygen). There is no direct electronic measurement for nitrogen but air content can be calculated by measuring the oxygen component. Also this measurement can separate the amount of air in the head space of a drink (that space that is not occupied by liquid) from the air in the beverage.

SPECIAL PROBLEMS (SPEED OF TEST AND INTERFERENCES)

The method of measuring a gas in summation, that is, a little at a time with a running total, in some cases is too slow. The reasons vary and are:
 (i) too much pressure build up from a competing gas,
 (ii) interference at the sensor by a competing gas,
 (iii) slow distribution of the gas in the measure chamber.

POLAROGRAPHIC SENSORS

A direct comparison can be made; that is, the ratio of air in the test mode to air in the calibration mode is the same as the ratio of oxygen in the test mode to oxygen in the calibration mode.

$$\frac{\text{AIR test}}{\text{AIR calibration}} = \frac{\text{OXYGEN test}}{\text{OXYGEN calibration}}$$

In a carbonated beverage there are primarily two forms of gas present. The desired gas is $CO_2$ and the undesirable gas is air. (A description of $CO_2$ measurement can be found in U.S. Pat. No. 4,607,342 which is hereby specifically incorporated by reference—Apparatus for Remotely Measuring and Controlling the Carbon Dioxide in a Beverage Liquid: On-Line). This invention measures the air content in the beverage which is ideally zero. There are several technologies employed to accomplish this measurement.

(i) The polarographic probe measures oxygen through a physical chemical process that converts oxygen to an electronic signal. The general equations are: At the gold cathode:

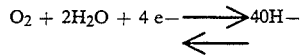

At the silver anode:

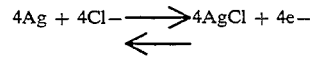

(ii) Ultrasonics is a conventional and convenient method of degassing a liquid. Air is less soluble than $CO_2$. The overwhelming amount of $CO_2$ in the liquid pushes the small amount of air out of the liquid and the head space and eventually into a test chamber above.

(iii) A microprocessor device provides control of the calibration and measuring sequences.

SPECIFIC SPECTRAL SENSORS

The specific $CO_2$ sensor is characterized by a self-calibrating device as described by Wong (U.S. Pat. No. 4,578,762 which is hereby specifically incorporated by reference). This device has been reduced in size and now is suitable for inclusion in a system that measures the $CO_2$ component in beverage gases, and environmental gases such as the $CO_2$ consumed by bacteria. Another type of oxygen device for measuring $O_2$ released by bacteria is a specific spectral device in the visible red (Wong U.S. Pat. No. 4,730,112 which is hereby specifically incorporated by reference). This has also been reduced in size so that it is suitable for instrumentation.

APPLICATIONS TO ENVIRONMENTAL FIELDS

These techniques can also be applied to some environment problems such as BOD (Biological Oxygen Demand) and bacteria nourishment in composting. In BOD measurements, the liquid sample of interest can be contained in a batching chamber and the oxygen gas (or specific gas component) can be removed by bubbling techniques. In composting, the compost heap can be considered a source of oxygen and $CO_2$ along with other gases.

BOD DEMAND

In certain circumstances, the quality of water is determined by its oxygen content. Most often the probes are placed directly in the liquid. However, by bubbling an inert gas through the liquid we will be able to remove oxygen to determine the biological oxygen demand and chemical oxygen demand. This is a direct outgrowth of the methodology for removing oxygen from a sealed container with no $CO_2$ or internal purge gas. The sealed container in this gas is a fixed volume of liquid that is contained in a "batching chamber" that has entrance and exit valves. When these valves are closed, the "batching chamber becomes a sealed container. An example of a batching chamber is described in Selden (U.S. Pat. No. 4,607,342 which is hereby specifically incorporated by reference).

COMPOSTING

A composting technique is at the center of many attempts to clean up the environment. The main gases that concern bacteria are $CO_2$ and $O_2$, and these gases to a large measure determine the activity of the bacteria which in turn determines how effectively they are eliminating (digesting) the pollutant of interest (gasoline, hydrocarbons, toxins, harmful metals, poisons, and pesticides). Normally the gas is measured flowing in a pipe.

BACKGROUND FOR DETERMINING BINARY MIXTURES IN A BEVERAGE GAS—PRINCIPALLY $N_2$ AND $CO_2$

The second major component in air is nitrogen. There is no specific spectral or polarographic method for measuring nitrogen gas. In certain beverages, a large amount of $N_2$ is added. If the system is basically a binary system, that is large amounts of $CO_2$ and $N_2$, then a double test will isolate the two gases. The two tests would be the non-specific pressure temperature test, sometimes referred to as the Heath test and a more specific $CO_2$ test. In some cases alternative degassing techniques must be used. In many cases an external gas will be bubbled through the liquid in the test container to expel the specific gas of interest.

The brewing industry in England adds nitrogen gas to their product for several reasons; one being that it "improves the quality of the head". Also low carbonation drinks need extra pressure internally in cans so that they will not collapse when piled on each other.

Since this device, as it is, analyzes two gases $CO_2$ (non-specific) and $O_2$(trace gas-specific), it is desirable to add an $N_2$ measurement to our instrument, because the non-specific $CO_2$ measurement is useless if large amounts of nitrogen are added. In many cases $N_2$ is added to the beverage so in that situation the $N_2$ content of the drink would have no relationship to the $O_2$ content (in air 4 to 1). The pressure-temperature (Heath) measurement is only valid in a one component system ($CO_2$). To analyze the two major gases ($CO_2$ and $N_2$—binary mixture), some existing technologies have been explored including molecular sieve, membrane, and several versions of thermal conductivity. These techniques all attempt to measure $N_2$ as such.

One method allows the gas to pass over a resistive element to measure the $CO_2/N_2$ mixture relative to 100% $CO_2$. The gas would be removed from the head space after agitation. The pressure-temperature (Heath) method will give us a total gas number, while the resistive element will give a relative number allowing us to determine the percent concentration for the binary system ($CO_2$ and $N_2$).

Another method for uniquely determining one of the two components in the binary mixture involves the well established technique of infrared absorption using one of the spectral lines of $CO_2$ (probably 4.3 microns). Neither $N_2$ nor $O_2$ have an infrared spectrum due to their symmetry ($O_2$ does have a slight spectrum in the far red near 0.79 microns).

Either one of these methods (or both)—thermal conductivity; $CO_2$ absorption—coupled with the additional information derived from the Heath (pressure/temperature) measurement (and additional mathematics) will allow the determination of each of the two components. The difference is that one method—thermal conductivity—is a non-spectral technique; which the second $CO_2$ absorption—is a specific spectral technique and is very precise. Basically, two equations in two unknowns are solved.

In summary, gases other than $CO_2$ and $O_2$ may be present in certain beverages. Usually this gas is nitrogen ($N_2$). Since our device measures $CO_2$ non-specifically (see U.S. Pat. No. 4,607,342 which is hereby specifically incorporated by reference) and $O_2$ (trace) specifically, we cannot separate $CO_2$ from $N_2$ (binary mixture) without another measurement. Also tertiary or greater mixtures of gases can be analyzed. Molecular sieves, membranes, and resistive techniques have been used for such separations. $CO_2$ absorption is another technique.

SUMMARY OF THE INVENTION

The purpose of this invention is to measure the air content in a carbonated beverage so that the test has the following advantages: (i) the test requires no dangerous chemicals, (ii) the test is electronic, (iii) the test is automatic so that no operator is required after the test is started.

Oxygen can be measured, for example, with a Clark or polarographic type cell (L. C. Clark J. Appl. Physiol., 6 189 (1953)) or by, for example, a Mancy or galvanic type cell (K. H. Mancy, D. A. Okun, and C. N. Reilley J. Electroanal. Chem., 4, 65 (1962)) Dissolved oxygen in a liquid normally is measured in the liquid state by such a probe. This invention removes the gas from the beverage (using ultrasonics, mechanical, or other means for degassing), deals with the special problems due to foaming, and provides an accurate calibration method and a repeatable result in close agreement with chemical tests. $CO_2$ can also be measured by potentiometric sensors using liquid electrolyte (Severinghaus, Bradley, J. Appl. Physiol. 13, 515 (1958)) or solid electrolyte (Maseen, Tierney, et.al. Conference of Solid State Sensors and Actuators 359 (1991)) as pH properties of the electrolyte change with the diffusing $CO_2$.

SPEED AND INTERFERENCES In order to shorten the time that it takes to complete a test or to eliminate non-oxygen (specific gas) interferents, several steps can be taken. These steps can be summarized as follows: (i) buffer solution to absorb unwanted gases and pressure, (ii) circulation, (iii) multi-chamber, (iv) vacuum, (v) compression and expansion.

BUFFER SOLUTION

An unwanted gas, a gas other than the specific gas that is being measured, may cause problems in several ways: first, the gas may directly interfere with the measuring process (example—chlorine and oxygen); second, there may be a chemical reaction in the electrolyte (polarographic sensors for example); and third, there may be an unwanted increase in pressure (in beverages, $CO_2$ creates most of the pressure while trace $O_2$ may be the gas of interest). An example of the latter two is NaOH, a buffer liquid in a buffer liquid chamber. The NaOH absorbs $CO_2$ and relieves the pressure in the measuring chamber. At the same time, a $CO_2$ interference to the electrolyte is avoided.

CIRCULATION

In many cases a circulator such as a fan will enhance the measurement by allowing a faster distribution of the gas in the measurement chamber.

MULTI-CHAMBER

This faster distribution is most important in a multi-chamber configuration. The advantage of a multi-chamber configuration is that the measurement can be accomplished with one "zeroing" or low measurement, and then each chamber filled individually to the point of maximum pressure, then chamber combined by adjoining values.

VACUUM

Another method to lower pressure is with a partial vacuum on the measure chamber. In some cases a side chamber must be used since the sensor will not respond properly in a vacuum. The side chamber is connected to the central measurement chamber by valves.

COMPRESSION AND EXPANSION (VARIABLE VOLUME CHAMBER)

In order to calibrate or confirm that a gas is the specific gas of interest, the size of the measure chamber or chambers can be expanded or reduced with a piston, balloon, or bellows. This allows the gas to be measured in two or more volumes. With a sensor or combination of sensors, two or more equations based on the ideal gas laws are created, which when solved, will identify interfering gases, and separate components of gases.

SPECIFIC $CO_2$ INFRARED ABSORPTION

An analysis can be made if the auxiliary measurement is $CO_2$ infrared absorption. In this case, the correction factor will be determined by developing a table of $CO_2$ gas present in the binary mixture as a function of temperature and pressure (the Heath variables). The temperature of the liquid is important but can be negated if the liquid sample temperature and the $CO_2$ sensor are at the same temperature, preferably room temperature (see Table 1).

|  |  | TEMP | PRES1 | VOL1 | PRES2 | VOL2 | SPECIFIC $CO_2$ SENSOR |
| --- | --- | --- | --- | --- | --- | --- | --- |
| 100% $CO_2$ | 1st pass | 68 | 45 | 4.20 | 13 | 1.64 | 1.00 |
|  | 2nd pass | 68 | 40 | 3.90 | 10 | 1.47 | 1.00 |
|  | 3rd pass | 68 | 35 | 3.60 | 7 | 1.29 | 1.00 |
| 95% | 1st pass | 68 | 45 | 4.20 | 13 | 1.64 | .90 |
|  | 2nd pass | 68 | 40 | 3.90 | 10 | 1.47 | .93 |
|  | 3rd pass | 68 | 35 | 3.60 | 7 | 1.29 | .98 |

In this case, the 1st temperature, the 1st pressure, and the 1st volume are the normal Heath type measurements; whereas the 2nd pressure and the 2nd volume are also Heath volumes in a larger chamber, correlated with the 1st volume. The ratio of the two volumes for 100% $CO_2$ will yield 1.00 when compared with the specific IR $CO_2$ reading. Variations from 1.00 would be predominantly nitrogen when that gas is also added to the beverage.

The relative solubilities are very important since $CO_2$ is approximately 30 times more soluble than $O_2$ which is about 2 times more soluble than $N_2$. Therefore, after more passes are made, the relative ratio based upon 100% $CO_2$ will approach that value.

BRIEF DESCRIPTION OF THE DRAWINGS

FIG. 5B—A retractable piercing needle with sensing elements for an automatic piercing needle in the pierced and sealed position.

DESCRIPTION OF THE DEVICE

Figure 1:
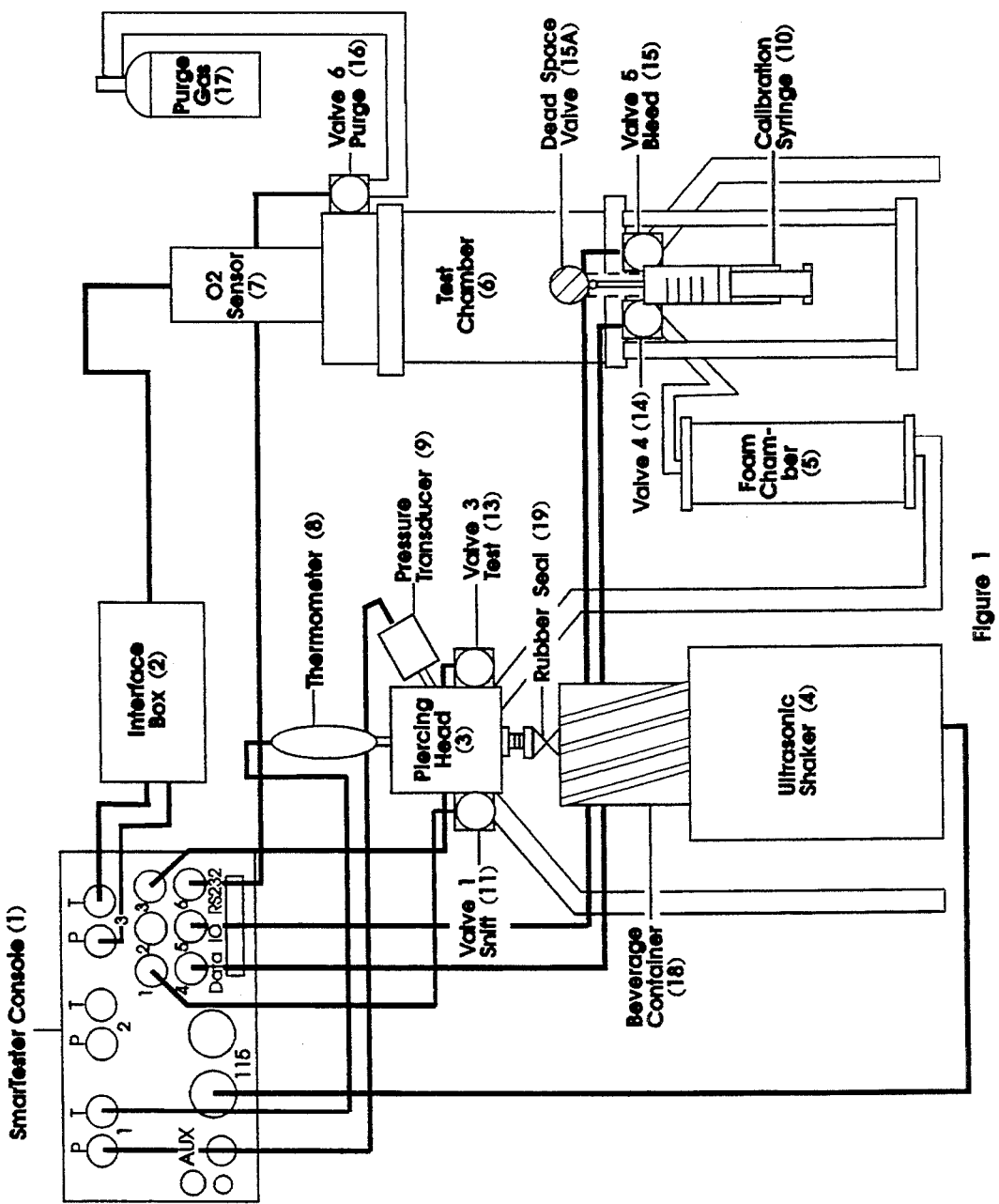
FIG. 1—A block diagram of the system for the measurement of air in a beverage liquid, including electrical and mechanical connections for air content test and a piercing head manifold.
Figure 2:
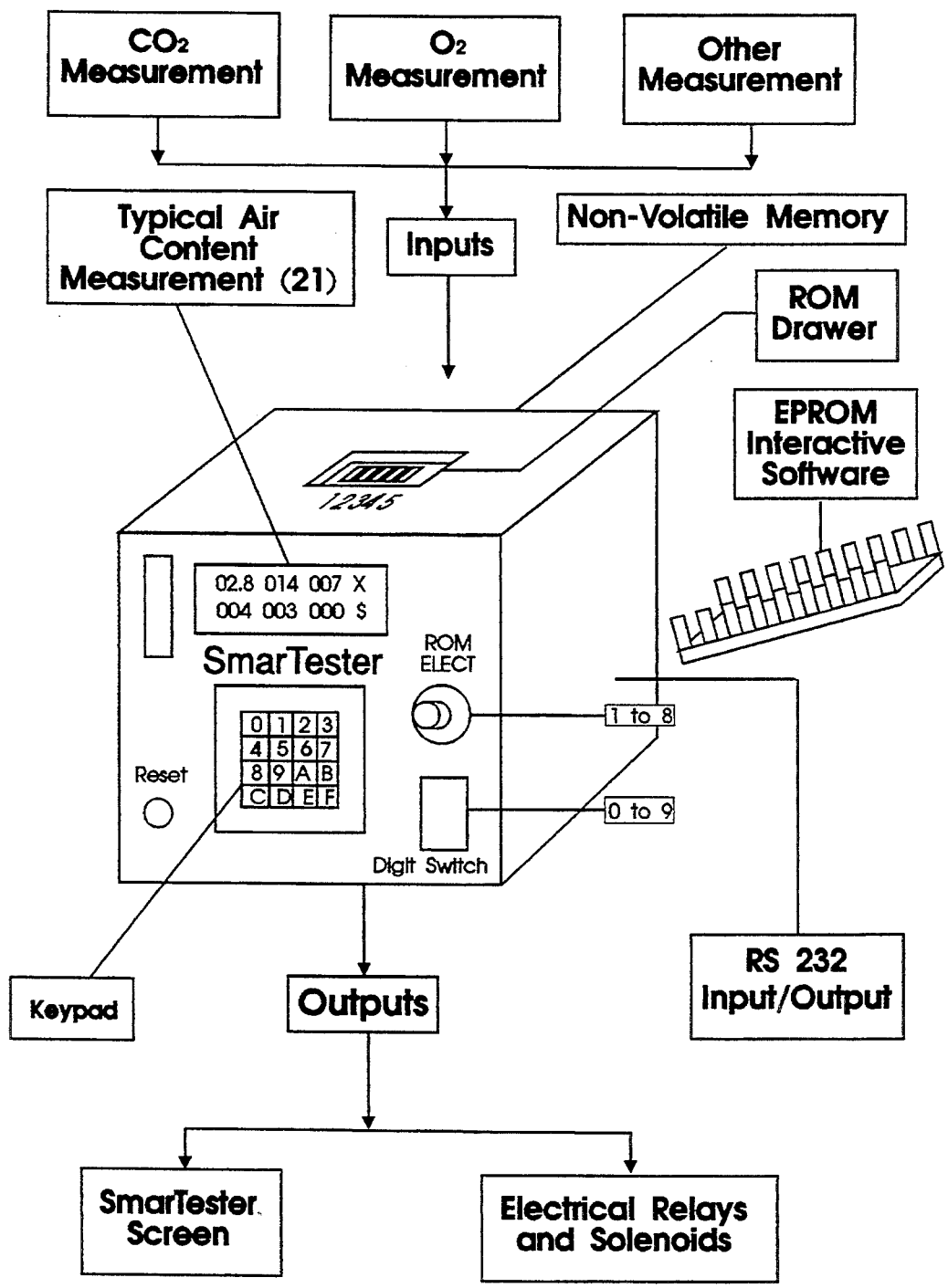
FIG. 2—A console that controls solenoid valves and allows for an oxygen measurement with display of partial oxygen measurements and their sum.

An apparatus to measure the air content in a beverage liquid is diagramed in (FIG. 1). The measurement is accomplished in two modes—the calibration mode and the test mode. This test can be achieved independently or in conjunction with a $CO_2$ test. All electrical connections are at the rear of the console (1). These connections are the control points for valves, ultrasonic devices, RS-232 communications, and electronic measuring probes—temperature (8), pressure (9), oxygen (7).

THE CALIBRATION MODE:

The most accurate method of calibrating any device is in the vicinity of the test result. The calibration syringe (10) can be opened to one of two positions (atmosphere and a test chamber) (6). The system (the test chamber, a foam chamber (5), and the associated valves and tubes) is purged of air (16) with a purge gas (17)—generally $N_2$ or $CO_2$. When the system is purged, the console saves and records the low end of the range. A calibration syringe (10) is open to atmosphere and pulled back to the required calibration point (usually 10 cc). The calibration syringe is then put into the second position via a mechanical dead space valve (15A); the syringe is depressed and the 10 cc's of air are now in the test chamber. At this point the high end range is measured, saved, and recorded.

THE TEST MODE:

A beverage container (FIGS. 1 and 7) (18) that is to be measured for air content is pierced by a hollow needle under a rubber seal (19) (see FIGS. 1, 4, 4A, 4B, 5, and 7 attached to a piercing device which applies a positive downward pressure. The piercing needle must go through several conditions: (i) rest (not in contact with the container), (ii) seal (rubber is firmly pressed on container without piercing), (iii) pierce (needle passes through container), (iv) stop (needle does not progress additionally into container).

Figure 4B:
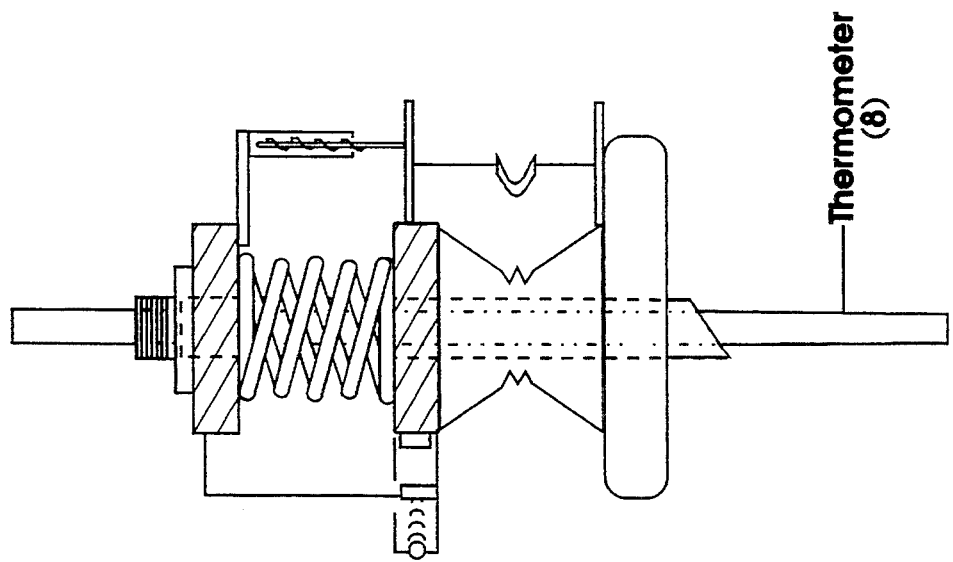
FIG. 4—A detailed view of a retractable spring-loaded piercing needle.
FIG. 4A—A retractable piercing needle with sensing elements for an automatic piercing device in the rest position FIG. 4B—A retractable piercing needle with sensing elements for an automatic piercing needle in the pierced and sealed position.
Figure 4A:
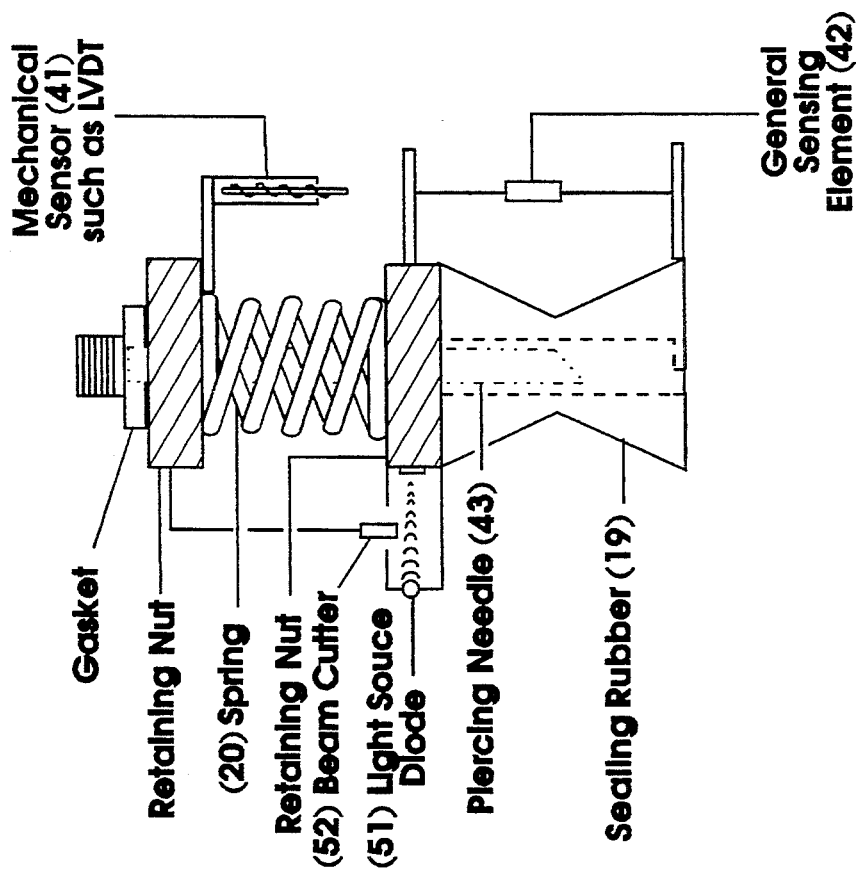

In the manual system, the operator can control these positions. In the automated system, the piercing needle assembly must be equipped with a detector that can send a signal back to the microprocessor or other similar electronic sensing device to give the status of the piercing needle. Two parts of the needle compress, the spring and the sealing rubber. These compressions can be measured in several ways, either singly or in combination, such as with a diode light source (51) and detector combination with a beam cutter (52), a mechanical position device, such as a linear vertical displacement transformer (LVDT) (41), or a strain gauge or resistive element. Alternatively, these detectors can be placed on the sealing rubber (19) as is seen in (FIGS 4 and 4A). The piercing needle mechanism in FIG. 4A is in the rest position and in the sealed/pierced position in (FIG. 4B).

Figure 3:
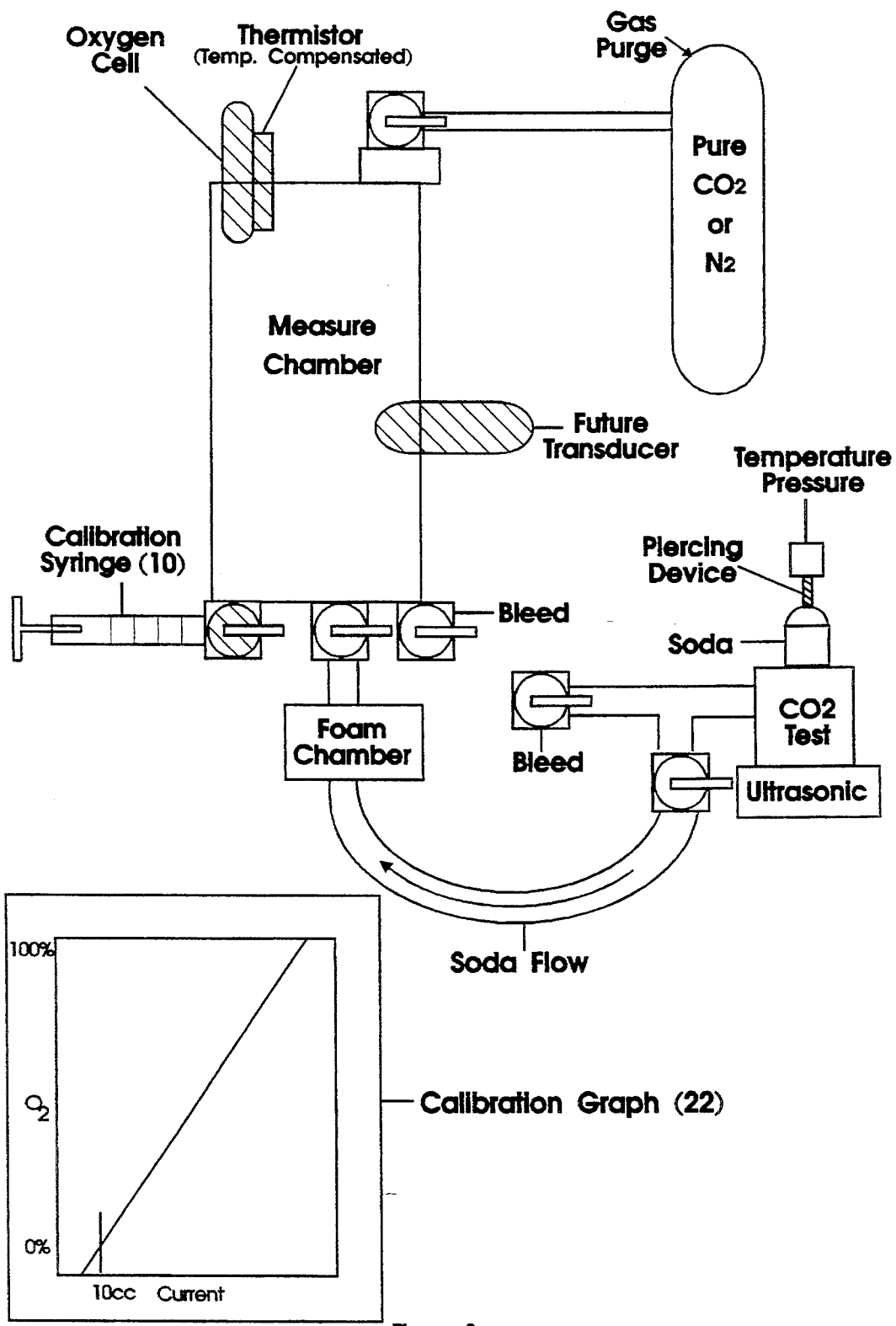
FIG. 3—A pictorial summary of the system with a graph that shows a calibration point.
Figure 5:
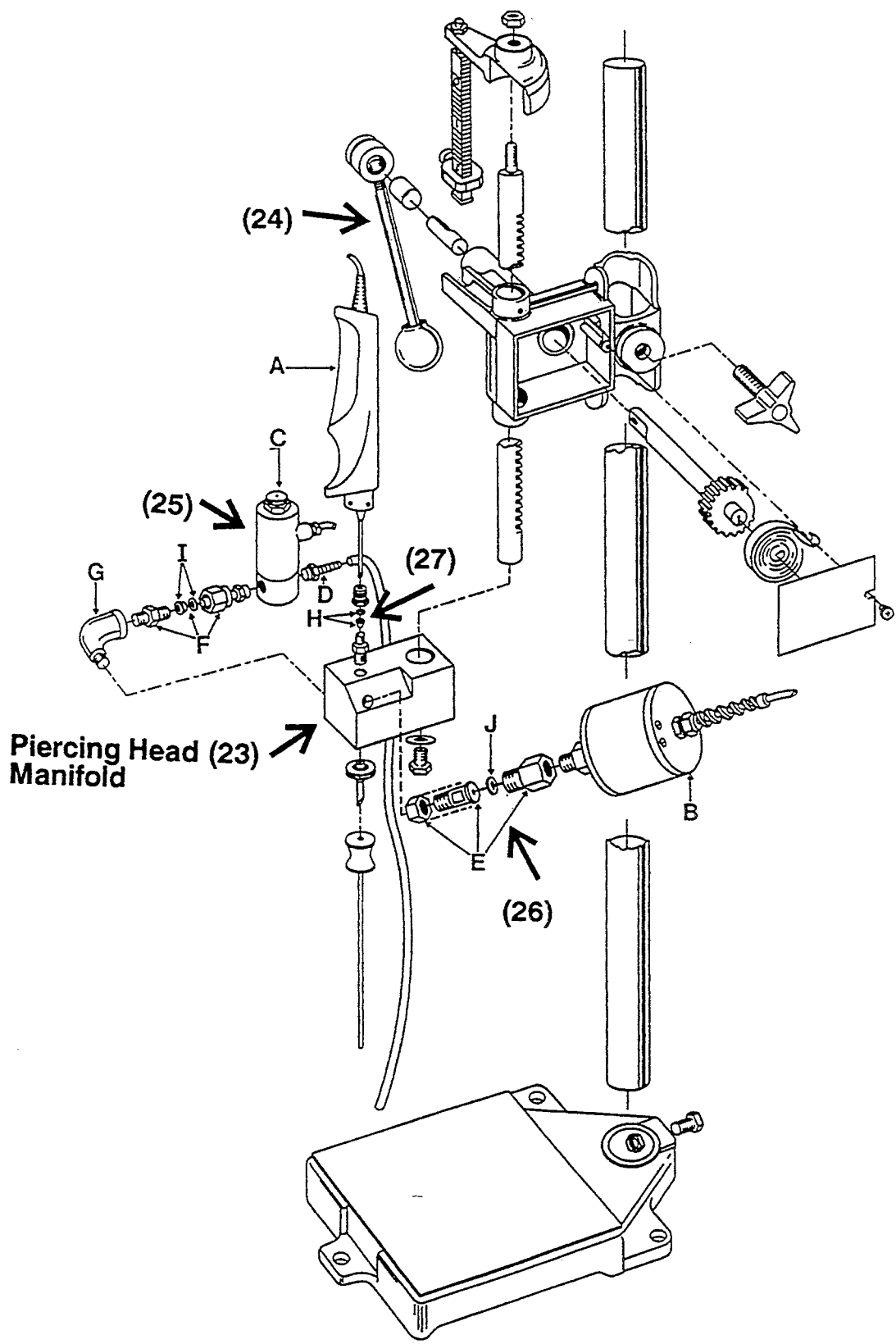
FIG. 5—Piercing head manifold attached to device that applies a positive downward pressure.
Figure 6:
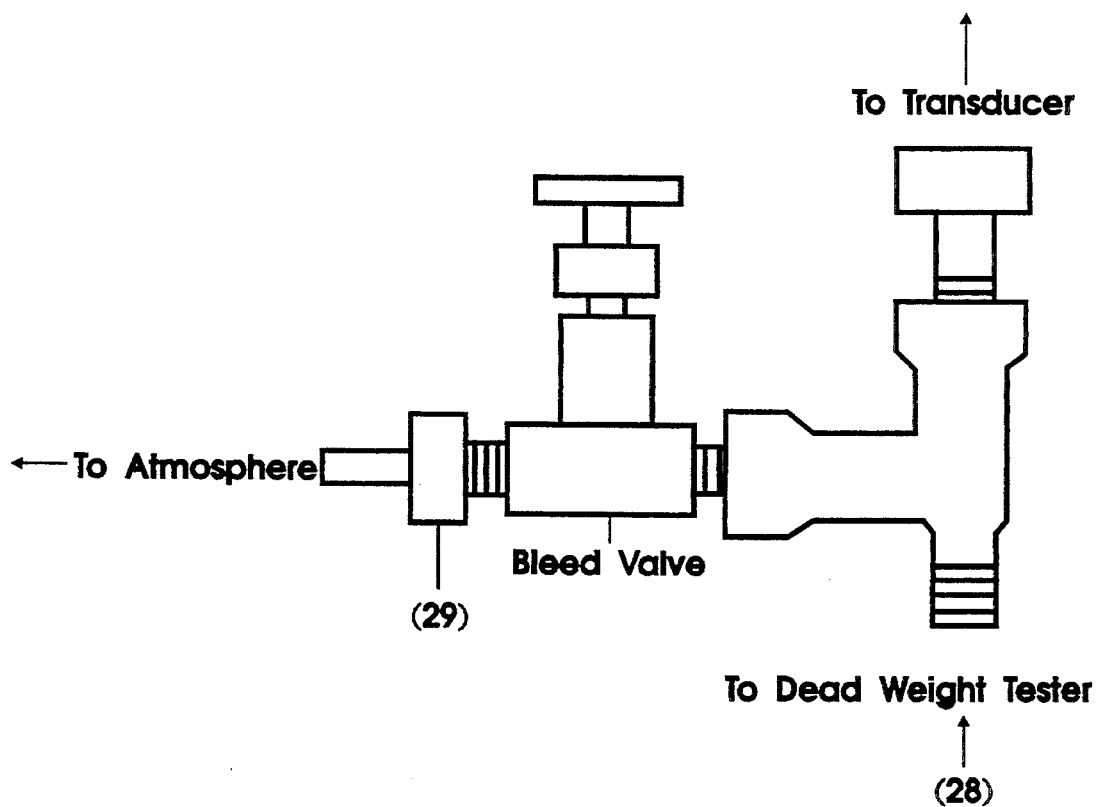
FIG. 6—Special fitting for dead weight tester.

The piercing head manifold (23) in (FIG. 5) is attached to a spring loaded device (24) that applies a permanent downward pressure and in turn holds the piercing needle and seal in place after the container is punctured. The manifold contains various internal pathways that allow the beverage gases and liquids to find their way to the proper part of the system. There is either one or two remotely or manually operated valves (25) that allow beverage gas to flow to the air content test or to be bled into the atmosphere. The pressure device is attached to the piercing head manifold by a special connector (26) in (FIG. 5). Another special connector (28) (see FIG. 6) with the same type of fitting (29) attaches to a dead weight tester. These fittings allow the pressure transducer to be easily removed from the manifold, to be easily attached to the dead weight tester, and opened to atmosphere for low end ranging. Also an electronic thermometer is attached to the manifold with a special seal (27). To prevent premature piercing of the container, a spring (FIGS. 4, 4A, 4B and 7) (20) is set above the sealing rubber so the rubber can be set on top of the beverage container without piercing the container. Piercing occurs when the positive downward pressure is applied. The piercing head (3) manifold (FIG. 1) which internally connects a thermometer (8), a pressure transducer (9), a snift or bleed valve (11), and a test valve (13) that allows the gas to flow to the foam chamber and the air test chamber. An ultrasonic device (4) is turned on for a finite time (3 to 10 sec.) and then off. (This cycle is repeated 3 to 5 times since all the air cannot be moved into the test chamber in one cycle because of the pressure and volume build up when degassing—an alternative would be several chambers and one pass.) This is a two part measurement; the first part of which is the zero or low end of the measurement; the second part is the raw measurement. The measurement in each cycle is the difference of the two.
MEASUREMENT (TEST GAS) PER CYCLE=RAW MEASUREMENT−ZERO MEASUREMENT Pressure build up is bled off at valve 5 (15) in preparation for the next cycle. The test chamber is a fixed volume cylinder and must remain so for the calibration to hold. A major difficulty arises from the fact that carbonated drinks foam when agitated (beer being generally worse than soft drinks). The foam chamber is placed between the beverage container and the test chamber to absorb the foam. If the foam or a portion of the liquid gets into the test chamber when the connecting valve (14) is open then its volume is decreased and the membrane at the tip of the oxygen probe can get wet. Both of these occurrences can affect the final result and must be avoided. The size of the test chamber, the size of the foam chamber, and the sensitivity of the oxygen probe (set at an interface box(2)) are all interrelated and are experimentally optimized. In the optimized situation 3 to 5 passes are required to get all of the air (normally 80% to 100% in 3 passes). The limitations are the pressure that the test chamber will reach and the pressure the oxygen probe will tolerate. A transducer will monitor this pressure; the pressure will tend to zero as the test is completed. (FIG. 12) shows the console and a display of the air content data. The data on the screen (21) indicates that there are 2.8 cc of air in the sample in 5 cycles or passes (2.8=1.4+0.7+0.4+0.3+0.0—Note missing decimal point in the partial results). FIG. 3 is a pictorial summary of the system. The graph (22) shows that the calibration is accomplished near the test point.

DETERMINATION OF SPECIFIC GASES IN BEVERAGES OR OTHER LIQUIDS THAT ARE NOT CARBONATED

Figure 7:
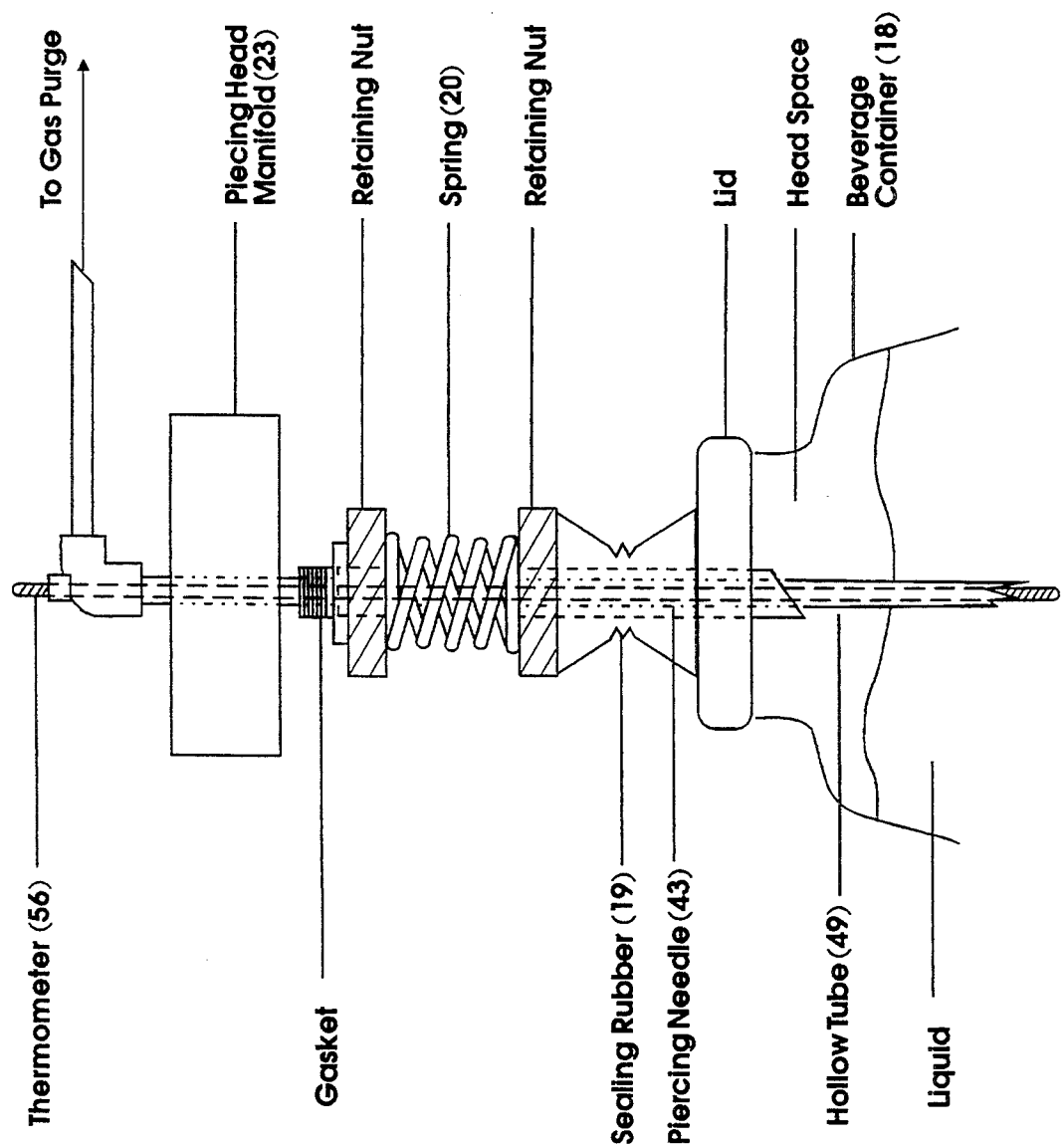
FIG. 7—External purge gas for removing specific gas component from a sealed container.

Internal carbonation pressure can be used to displace or force $O_2$ or another specific gas into a test chamber to be measured by a polarographic sensor, such as an oxygen sensor, or a specific gas spectral sensor, such as an infrared sensor. However, some beverages are lightly carbonated or not carbonated at all. In these cases the purge gas (17) must be supplied directly to the liquid in the sealed container to complete the degassing of a specific component gas. The external purge gas will supplement any internal gases that would degas with ultrasonics or other mechanical agitations. The entrance for the external gas into the liquid is through the piercing needle (43). The desired result will be realized by bubbling gas into the non-carbonated or lightly carbonated liquid through the piercing needle (input for temperature probe) using a double-tubing technique; that is, a hollow tube would enter the liquid and would be inserted between the piercing needle and temperature probe (56) as is seen in (FIG. 7). If the temperature of the liquid is not important then the degassing hollowed tube would be inserted alone through the piercing needle. In this manner, a degassing gas would be bubbled into the liquid, hence displacing the specific component gas such as $O_2$ and sending that gas into the measurement chamber. In this way any liquid can be analyzed for dissolved oxygen (or other specific gas) content by removing the oxygen from the liquid with another gas (such as CO2) that can be introduced from an auxiliary outside source.

DETERMINATION OF $N_2$ USING A DOUBLE $CO_2$ MEASUREMENT AND REPLACING THE HEATH METHOD WITH A SPECIFIC INFRARED MEASUREMENT

Figure 8:
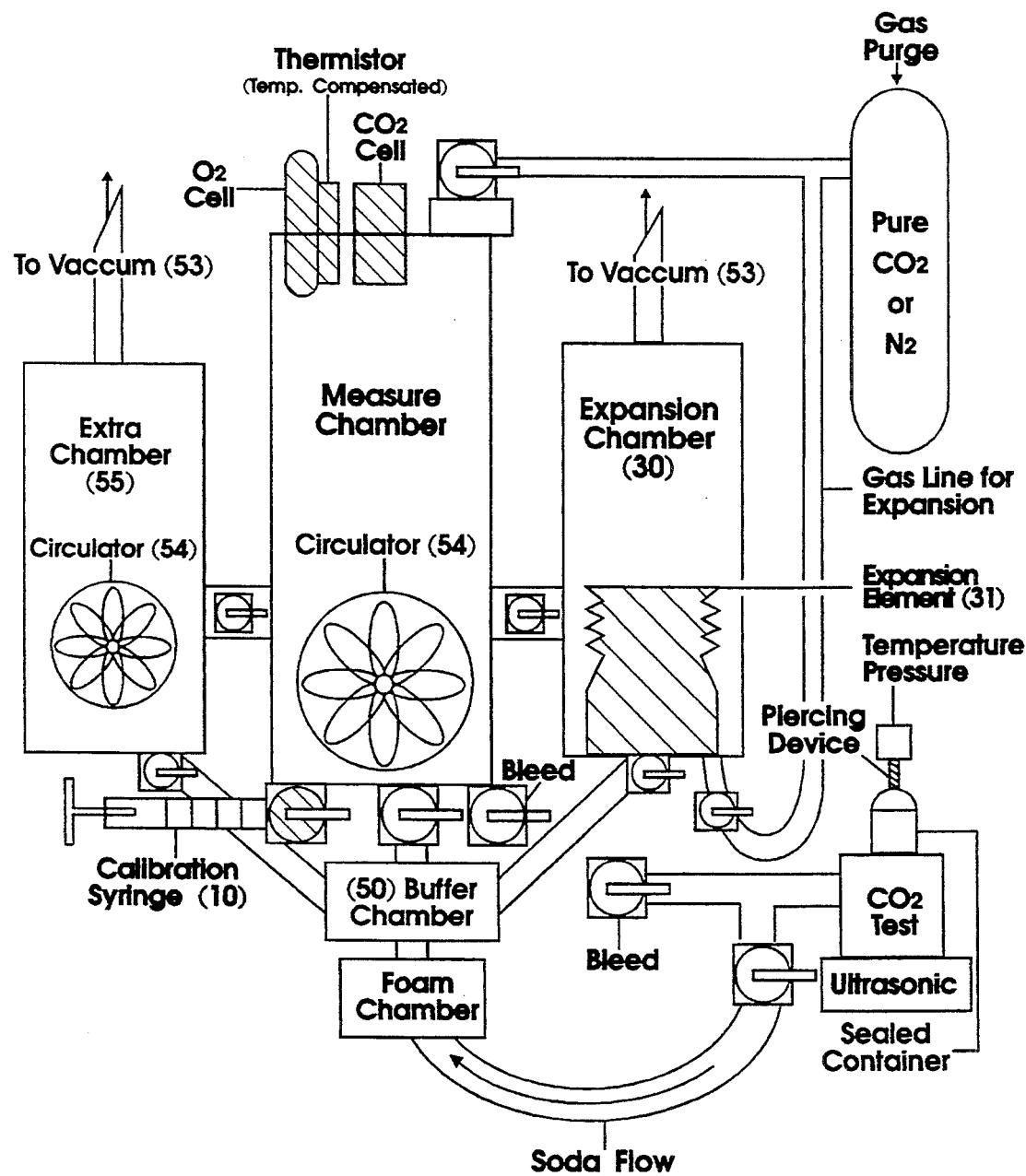
FIG. 8—General system for controlling speed of test and interferents.
Figure 8A:
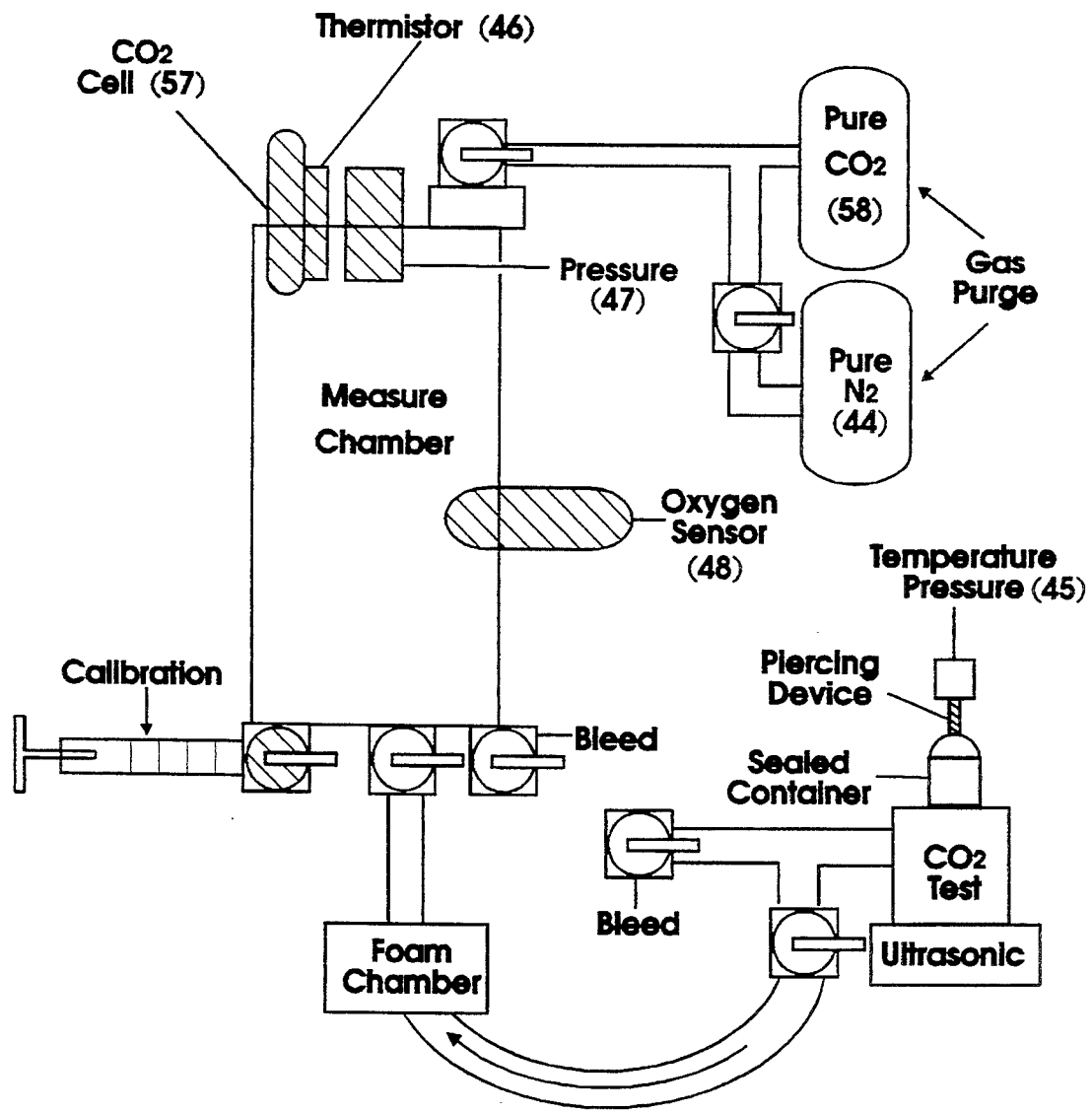
FIG. 8A—Configuration for determining mixtures of gases

The non-specific measurement of Heath (45) (Pressure/Temperature Volume) is coupled with the IR measurement of Wong to determine the unmeasurable component of the binary mixture, that is $N_2$. (See FIG. 8A) The pressure (47) and temperature (46) are also measured in the measure chamber. These two sensors are used to calibrate the specific $CO_2$ sensor (57) as seen in (FIG. 8A) with pure $CO_2$ (58) and to create a second reference chart to compare to the Heath chart. The $N_2$ gas is used to purge (44) the chamber of old $CO_2$ and $O_2$. In addition, if large amounts of $O_2$ are present, that measurement can be made independently (48) to separate the $CO_2$, the $O_2$, and $N_2$ into a measurable tertiary mixture. The $CO_2$ sensor alone can be used to totally replace the Heath method if $CO_2$ is the only gas of interest using a new set of charts in a convenient measure chamber.

SYSTEM FOR CONTROLLING SPEED OF TEST AND INTERFERENTS

The system (FIG. 8) has a number of components that can be used individually or in combination. The buffer chamber (50) sits above the foam chamber. The purpose is to eliminate unwanted gases from the system. These gases act as interferences with the normal measurement either by directly affecting the specific gas sensor or increasing the pressure in the measure chamber. The buffer may be in a liquid such as NaOH which absorbs $CO_2$ or a membrane or a molecular sieve.

The measure chamber must have a steady state distribution of gas to make an accurate measurement. The mixture becomes more uniform as the gas is circulated by a fan (54) or a similar device. In addition, for the proper operation, many gas sensors, particularly membrane sensors, a certain level of circulation must be maintained. In order to enhance the flow of gas from the sealed container, a partial vacuum (53) may be used. The normal atmosphere of gas that is present is more quickly replaced by the gas in the sealed container. An extra chamber (55) or chambers can be used to reduce the number of partial cycles necessary to make a measurement. In a single chamber, the measurement often requires a new zero measurement before each partial measurement. The multi-chamber approach allows the system to not be pressure limited, hence eliminating the need for multi-zero and therefore increasing the speed of the measurement.

The expansion chamber (30) allows the volume of the system to be changed—that is, expanded or contracted. This allows the test to be measured under different conditions (various volumes). In this way the system can be quickly calibrated by a percent change of a known amount of gas. Also the presence of interferents can be determined by observing the proportional sensor readings as a function of volume. The expansion element may be a balloon, a bellows, or a piston (31).

OXYGEN DEMAND

Figure 9:
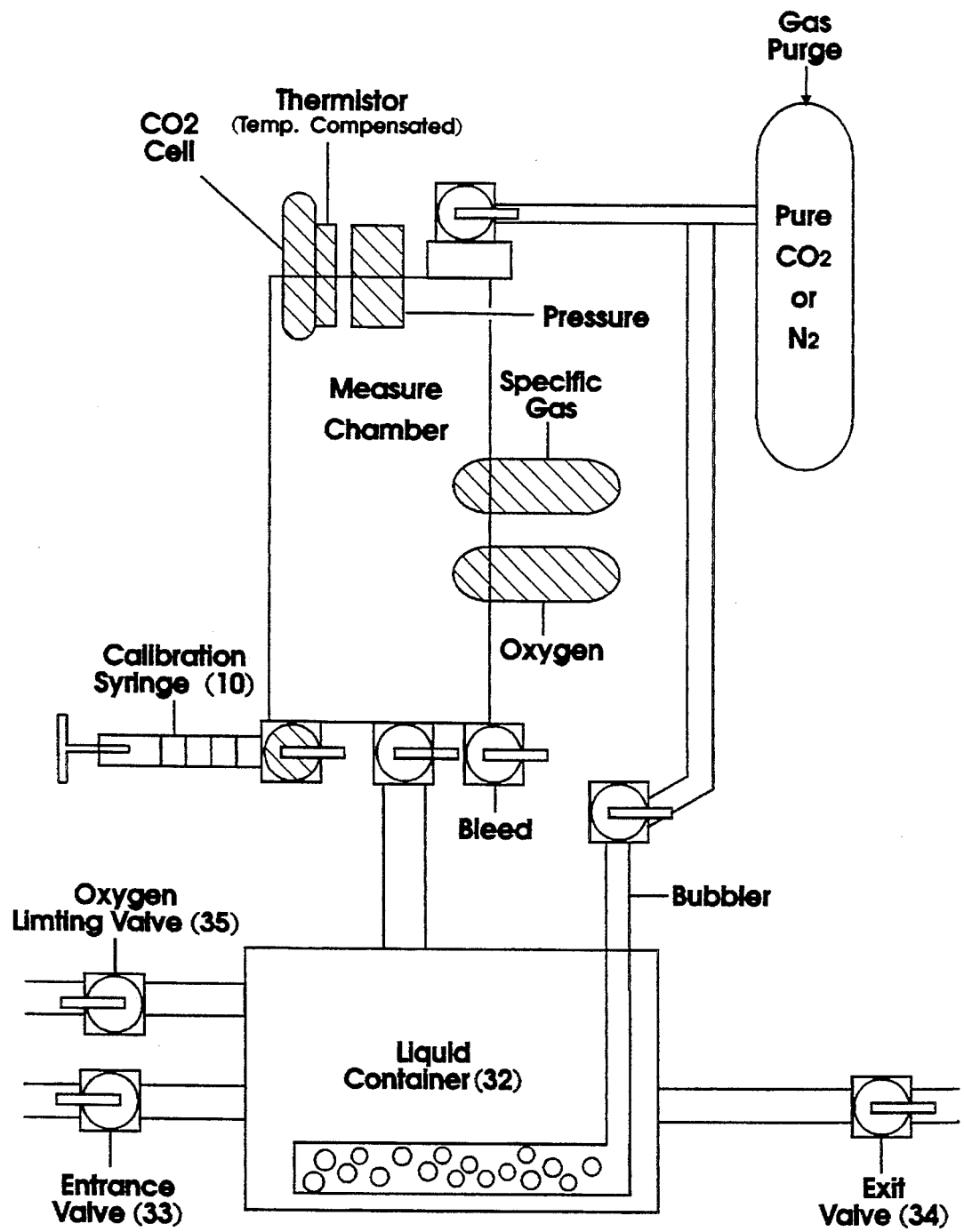
FIG. 9—System for BOD and COD measurements.

BOD, COD, or straight oxygen measurements (FIG. 9) can be completed in several ways. The unique part of this test is that the oxygen measurement is completed in the gas state in the measure chamber. This prevents sensor fouling which is a major limitation for many, many sensors. One technique is to allow the liquid of interest to be batched (32) and the oxygen to be purged into the measure chamber by a bubbler. For enhanced BOD and COD measurements, a pure liquid can be batched in the liquid container (32) between the entrance (33) and exit (34) valves. The contaminated liquid is introduced when the oxygen limiting valve (35) is opened. Since the pure liquid has a known amount of oxygen (normally 10 mg/liter at STP), the rate of consumption can be determined by bubbling purge gas into the liquid container after a set amount of time. The decline in oxygen content from 10 mg/liter is a measure of the BOD/COD demand of the contaminated or oxygen limiting liquid.

COMPOSTING

Figure 10:
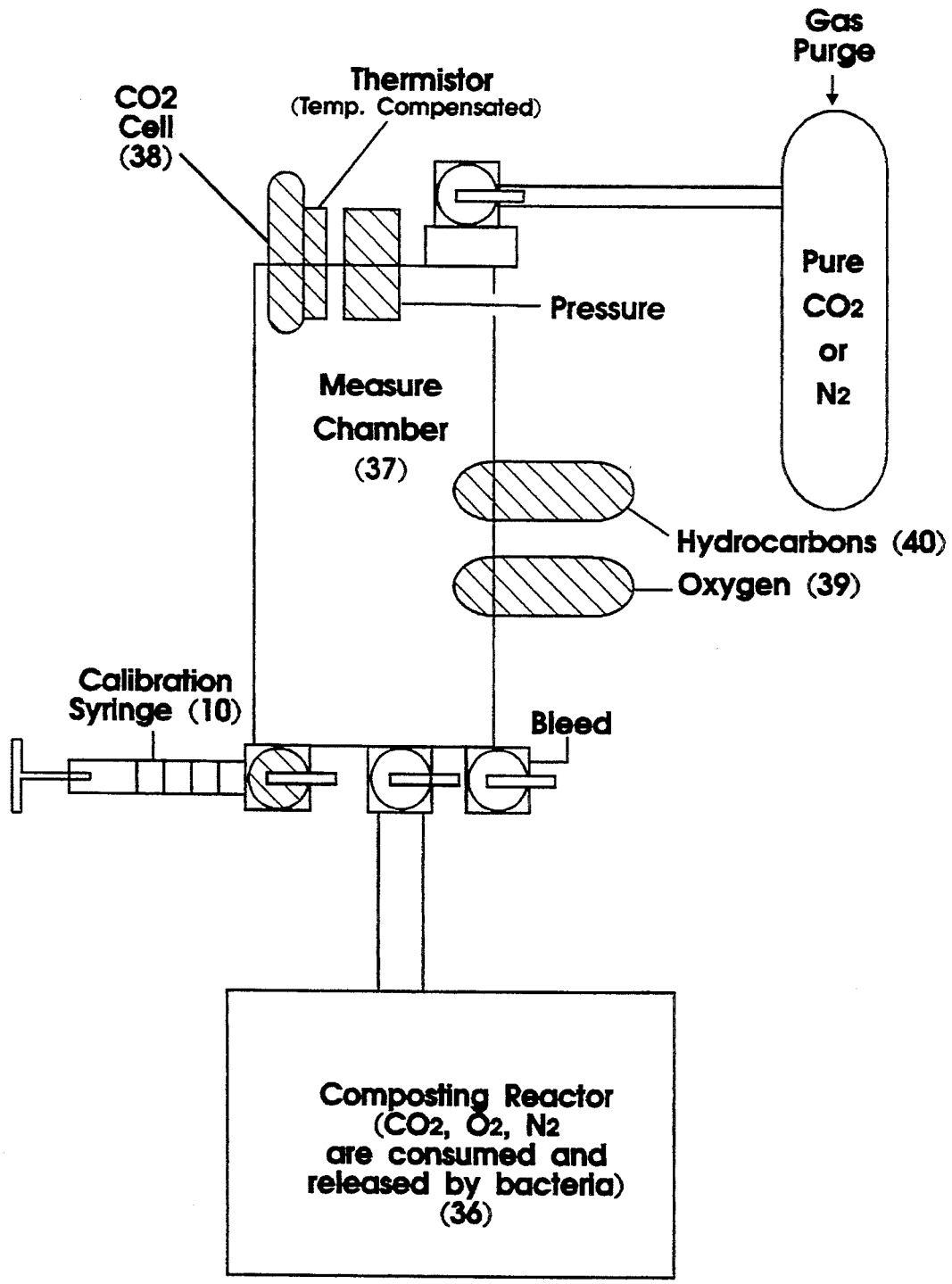
FIG. 10—System for bacteria respiration.

Another application of testing gas is a measure chamber that sits on top of a composting heap (37) (FIG. 10). The bacteria generally releases oxygen and consumes $CO_2$. By periodically opening the solenoid valve that connects the measure chamber to the compost reactor, the status of the bacteria (36) can be monitored by measuring the CO2 (38) to oxygen (39) ratio. In addition, other gases are often present in the form of hydrocarbons (40) which can be a measure of how rapidly the contaminate is being removed from the soil and the status of the composting reactor.

We claim:

1. A device for measuring an amount of a gas in a sealed container of fluid comprised of:
    a) a piercing mechanism for piercing the sealed container;
    b) a degassing mechanism connected to the piercing mechanism selected from the group consisting of ultrasonics, mechanical devices, electrical devices, and purge gases for releasing a component of the gas included in a mixture of gases released from the pierced container;
    c) a test chamber which receives the component of released gas to be measured in the released mixture of gases which passes through at least one additional chamber, selected from the group consisting of a foam chamber, an expansion chamber, a buffer chamber, an extra test chamber and a combination thereof; and
    d) a gas specific sensor, which measures the amount of the component of the released mixture of gases in the test chamber.

2. The device of claim 1 wherein the piercing mechanism is a retractable piercing needle such that the compression for the piercing needle is monitored in a rest position, a sealed position, a sealed and pierced position, and a stop position by a device selected from the group consisting of a light sensing device and a mechanical position device.

3. The device of claim 1 further comprising an auxiliary hollow tube inserted either alone or in combination with a thermometer into the container to allow the introduction of an external gas to remove a specific gas component from the fluid.

4. The device of claim 1 further comprised of a buffer chamber before the test chamber that contains a buffer which is selected from the group consisting of a liquid, a membrane, and a molecular sieve, to remove unwanted gases, in the released mixture of gases, that interfere with the measurement of the component of the released mixture of gases.

5. The device of claim 1 wherein the test chamber or the extra chamber contains a circulator to increase the steady state distribution speed of the gas component.

6. The device of claim 1 further comprising an expansion chamber attached to another chamber selected from the group consisting of the test chamber, the extra chamber, the foam chamber and the pierced container wherein the pressure of the test chamber is effectively changed for concentrating the component of the released mixture of gases to be measured.

7. The device of claim 1 further comprising a vacuum attached to the test chamber to remove at least some of the atmosphere in the chamber.

8. The device of claim 1 further comprising a pressure sensor to measure $CO_2$ variations.

9. The device of claim 1 further comprising an extra test chamber or multi-test chambers attached to the test chamber that can be opened to relieve the pressure in the test chamber or can be utilized for calibration.

10. A method for measuring at least one gas in a mixture of gases in a sealed container of fluid comprising the steps of:
    a) piercing the sealed container with a piercing mechanism;
    b) degassing the pierced container to release the mixture of gases;
    c) passing the released gases into a test chamber attached to at least one additional chamber that reduces interference with the measuring process; and d) measuring the amount of the at least one gas in the released mixture of gases.

11. The method of claim 10 wherein two tests are completed for a binary mixture of gases such that the first test is a test for non-specific gas volumes and the second test is an infrared test for the first gas resulting in a mathematical formulation that allows for the determination of the amount of the second gas for which there is no specific measurement.

12. The method of claim 10 wherein the at least one gas to be measured is selected from the group consisting of $CO_2$, $O_2$, and $N_2$, that combines the non-specific measurement with a specific IR measurement of $CO_2$ and a specific measurement of $O_2$ to separate the tertiary mixture into the individual components of $CO_2$, $O_2$, and determining the amount of $N_2$.

13. A method for measuring a mixture of gases in a closed container of fluid comprising the steps of:
   a) degassing the closed container, after it is opened, to release the mixture of gases containing one or more gas components to be measured;
   b) passing the released gases into a test chamber attached to one or more additional chambers that reduce interferences due to pressure build-up or that reduce interference from undesirable gases that interfere with the measuring process; and
   c) measuring an amount of the one or more gases in the released mixture of gases.

14. The method of claim 13 wherein a container of liquid is degassed by a bubbling means and tested for oxygen content so that the gas passes into the test chamber through a gas inlet valve so that oxygen content of the liquid in the container can be measured.

15. A method of measuring a mixture of gases from a closed container that is a bio-reactor selected from the group consisting of composting reactors and bio-slurry reactors such that when opened releases $CO_2$, $O_2$, and other gases that are consumed and released by bacteria inside of the reactor, to indicate status of the bacteria in the reactor comprising the steps of:
   a) flowing oxygen and $CO_2$ from the reactor, when opened, into a constant volume test chamber containing a specific gas sensor;
   b) measuring the oxygen content and the $CO_2$ content; and
   c) using the measured amount of the gases to indicate the status of the bacteria in the reactor.

16. The method of claim 15 further comprising at least one hydrocarbon sensor to detect hydrocarbon gas as an indication of the status of the bacteria in the reactor.

17. A method for measuring an amount of a gas in a sealed container of fluid comprising the steps of:
   a) piercing the sealed container with a piercing mechanism;
   b) degassing the pierced container with a degassing mechanism connected to the piercing mechanism selected from the group of ultrasonics, mechanical devices, electrical devices, and purge gases, wherein said degassing mechanism releases a component of the gas included in a mixture of gases released from the pierced sealed container;
   c) receiving the component of the released mixture of gases in a test chamber and passing the component through at least one additional chamber, selected from the group consisting of a foam chamber, an expansion chamber, a buffer chamber, an extra test chamber and a combination thereof; and
   d) measuring an amount of the component of the released mixture of gases in the test chamber with a gas specific sensor.

18. The method of claim 17 wherein the piercing mechanism is a retractable piercing needle such that the compression for the piercing needle is monitored in a rest position, a sealed position, a sealed and pierced position, and a stop position by a device selected from the group consisting of a light sensing device and a mechanical position device.

19. The method of claim 17 further comprising the step of inserting an auxiliary hollow tube with a thermometer into the container to allow the introduction of an external gas to remove the component of the released mixture of gasses.

20. The method of claim 17 further comprising the step of passing the released gas through a buffer chamber placed before the test chamber that contains a buffer selected from the group consisting of a liquid, a membrane, and a molecular sieve, to remove unwanted gases, in the released mixture of gases, that interfere with the measurement of the specific component of gas.

21. The method of claim 17 further comprising the step of passing the released mixture of gases through an expansion chamber attached to a member of the group selected from the test chamber, the extra chamber, the foam chamber and the pierced container, wherein pressure of the test chamber is effectively changed for concentrating the component of the released mixture of gasses that is to be measured.

22. The method of claim 17 further comprising the step of subjecting the test chamber to a vacuum to remove at least some of the atmosphere in the chamber.

23. The method of claim 17 further comprising the step of determining pressure of the released mixture of gases to measure $CO_2$ variations.

24. The method of claim 17 further comprising the step of passing the mixture of released gases through a chamber selected from the group consisting of an extra test chamber and multi-test chambers that is attached to the test chamber that can be opened to relieve pressure in the test chamber.

25. The method of claim 24 wherein the test chamber or the extra chamber contains a circulator to increase steady state distribution speed of the specific gas component.

* * * * *